United States Patent [19]

Kajfez et al.

[11] 4,160,096

[45] Jul. 3, 1979

[54] PROCESS FOR PRODUCTION OF 5-NITROIMIDAZOLE DERIVATIVES

[75] Inventors: Franjo Kajfez; Vitomir Sunjic; Vesna Sunjic, all of Chiasso, Switzerland

[73] Assignee: CRC Compagnia di Ricerca Cimica S.A., Chiasso, Switzerland

[21] Appl. No.: 928,832

[22] Filed: Jul. 27, 1978

Related U.S. Application Data

[63] Continuation of Ser. No. 720,613, Sep. 3, 1976, which is a continuation of Ser. No. 569,383, Apr. 18, 1975, abandoned.

[30] Foreign Application Priority Data

Apr. 19, 1974 [CH] Switzerland ............... 5459/74

[51] Int. Cl.² ........................................... C07D 233/94
[52] U.S. Cl. ................................................ 548/338
[58] Field of Search ....................................... 548/338

[56] References Cited

U.S. PATENT DOCUMENTS

| | | | |
|---|---|---|---|
| 3,444,175 | 5/1969 | Shen et al. | 260/309 |
| 3,689,567 | 9/1972 | Shen et al. | 260/607 AR |

FOREIGN PATENT DOCUMENTS 1526002  4/1968  France ................... 260/607 A

OTHER PUBLICATIONS

Houben-Weyl, Methoden der Organischen Chemie, Schefel-Selen-Tellur-Verbindungen, pp. 231–233 & 240–241, Stuttgart, Thieme, 1955.
Suter, The Organic Chemistry of Sulfur Tetracovalent Sulfur Compounds, pp. 667–673, N. Y., Wiley, 1944.
Wagner et al., Synthetic Organic Chemistry, pp. 801–803 & 821, N. Y., Wiley, 1953.
Caplar et al., J. Het. Chem., Dec. 1974, vol. 11, pp. 1055–1060.

*Primary Examiner*—Natalie Trousof
*Assistant Examiner*—Robert C. Whittenbaugh
*Attorney, Agent, or Firm*—Haseltine, Lake & Waters

[57] ABSTRACT

A process for preparing 5-nitroimidazole compounds of

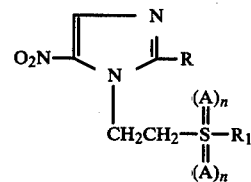

where R and $R_1$ are each alkyl from 1 to 4 carbon atoms, A is oxygen and n is 1, allowing for improved yields of the final products, is described.

3 Claims, No Drawings

PROCESS FOR PRODUCTION OF 5-NITROIMIDAZOLE DERIVATIVES

This is a continuation of U.S. patent application Ser. No. 720,613, filed Sept. 3, 1976 which, in turn, is a continuation of U.S. patent application Ser. No. 569,383, filed Apr. 18, 1975, now abandoned.

The present invention relates to a new process for the manufacture of 5-nitroimidazole derivatives having the general formula I below:

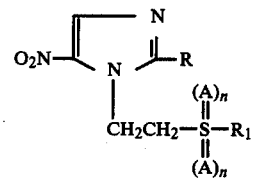

wherein
R is alkyl having 1–4 carbon atoms,
$R_1$ is alkyl hydrogen, an alkali or alkaline earth metal, alkyl having 1–4 carbon atoms,
a is oxygen, and
n is 1.

The compounds having the general formula I are obtained through the conversion of compounds having the general formula II below:

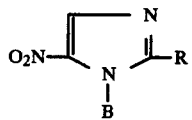

wherein:
R is as defined in Formula I, B is a 2'-haloethyl group (—$CH_2CH_2Hal$), where Hal is a halogen, or an ethyl sulfino group (—$CH_2CH_2SO_2N$), in the form of its alkali or alkaline earth salt,
with compounds having the general formula III below:

wherein:
Z is a sulfino group —($SO_2H$), in the form of an alkali or alkaline earth salt, or halogen; however, Z must be different from group B in Formula II; (for example, when B is —$CH_2CH_2SO_2Na$ and Z is a halogen atom, or when B is —$CH_2CH_2Hal$ and Z is —$SO_2H$), and $R_1$ is as defined above.

The process of the present invention preferably is carried out in an inert solvent medium such as dimethylformamide, acetonitrile, dimethylsulfoxide and the like, usually at its boiling temperature or somewhat lower, and is suitably even at room temperature.

The process of making compounds having the general Formula I according to the invention provides high yields, of a high-purity product.

Compounds having general Formula II have been described previously in the literature. (F. Kajfez, Journal of Medical Chemistry 11, 167 (1968), including compounds in which B is —$CH_2CH_2Br$, or —$CH_2CH_2I$).

Compounds having the general Formula I exert an antiparasitic and bactericidal effect in the human body. Thereby they are utilized for the treatment diseases caused by parasites such as trichomonas or amoebas and have the big advantage over other nitroimidazoles in that they can be administered orally.

The invention will now be illustrated with reference to the following Examples which are not intended in any manner to restrict the scope of present invention.

EXAMPLE 1

Preparation of Intermediates

Sodium and Barium 1-(2'-Ethylsulfonate)-2-Methyl-5-Nitroimidazole 4.68 g. (20 m moles) of 1-(2'-bromoethyl)-2-methyl-5-nitroimidazole (M.P. 78°–80° C.) is added to 2.90 g. (23 m moles) of $Na_2SO_3$ dissolved in 20 ml. water and 6 ml. ethanol. The reaction mixture is heated to 60°–65° C. to effect complete dissolution. Stirring at this temperature is continued for 12 hours whereafter 1.26 g. of $Na_2SO_3$ is added. After 2 hours the reaction is complete and the reaction mixture is evaporated to dryness. The residue, which is extremely hygroscopic, is a mixture of the inorganic salt and the sodium salt of the product. This sodium salt then is dried twice with 30 ml. portions of acetonitrile, and used for the manufacture of the compound in Example 5.

The hygroscopic acid is identified by formation of its barium salt, by reaction with barium hydroxide, which precipitates as a gray-white substance, and disintegrates upon heating at 250° C.

Analysis: $C_{12}H_{16}N_6O_{10}S_2Ba$ —
Calculated: 32' 22.68%.
Found: Ba' 22.20%.

Ir (KBr): 2990, 2950, 1522, 1475, 1450, 1255, 1230, 1090, 878, 822, 740 $cm^{-1}$.

EXAMPLE 2:

1-[2'-(Ethylsulfonyl)-Ethyl]-2-Methyl-5-Nitroimidazole

To 7.5 of the dried crude product of Example 1 is added 50 ml. of $SOCl_2$ and 2 ml. of dimethylformamide. The mixture then is heated under reflux for 4 hours. Thereafter the $SOCl_2$ is evaporated and the residue extracted twice with 20 ml. portions of benzene. The residue then is separated into aqueous and organic phases by extraction with 200 g. of ice water and 3 × 100 ml. portions of chloroform. The chloroform extract is dried over sodium sulfate, filtered and the solvent is removed. The residue consists of the pure acid chloride (2.95 g), which is dissolved in dioxane, an inert solvent which is missible with water. This solution then is added dropwise under cooling by an ice-salt bath into a suspension of 3.2 g. of zinc dust in 5 ml. water and 5 g. of ice. The temperature was held to below +5° C. After 3 hours the reaction is complete. The reaction mixture then is added dropwise during an hour into a solution of 3.5 g $Na_2CO_3$ in 15 ml. of water which is heated to 85° C. The hot solution then is filtered, and the residue is washed with warm water. The clear filtrate is evaporated to dryness under vacuum. To the solid residue is added 20 ml. of dimethylsulfoxide and 7 ml. of ethyl bromide, and the mixture is heated to 120° C. for 3 hours under reflux. The solvent is removed and the residue is suspended in water and filtered. The residue thus obtained is recrystallized from ethanol to produce 1.72 g of 1-[2'-ethylsulfonyl)-ethyl]-2-methyl-5-nitroimidazole. (M.P. 124°–126° C.) The compound is identical with the compound made in Examples 3 and 6.

After completion of the reaction, the product is neutralized with $Ba(OH)_2$, $Pb(OH)_3$ or $Mn(OH)_2$, to provide salts of the product, which then are separated from the reaction mixture.

The yield is improved when the reaction is carried out with ethyl bromide and pure salts of the 1-(2'-ethylsulfonyl)-2-methyl-5-nitroimidazole, then if one proceeded without isolating the sulfinic acid salts.

EXAMPLE 3

1-(2'-(ethylsulfonyl)-Ethyl]-2-Methyl-5-Nitroimidazole 5.83 g. (25 m moles) of 1-(2'-bromoethyl)-2-methyl-5-nitroimidazole is dissolved in 50 ml. of dimethylsulfoxide and 5.48 g. (30 m mole) of the sodium salt of ethyl sulfinic acid ($CH_3CH_2SO_2Na$) is added. The reaction mixture is maintained for 2½ hours at 100°-110° C. thereafter the solvent is removed under vacuum and the solid residue is washed with water and recrystallized from ethanol. The yield is 2.28 (37%) of 1-[2'-(ethylsulfonyl)-ethyl]-2-methyl-5-nitroimidazole, M.P. 124°-126° C.

Analysis: $C_8H_{15}N_3O_4S$ (MW=247.3)—
Calculated: C:38.86, H:5.30, N:16.99, S:12.97%.
Found: C: 38.69, H:5.42, N:18.21, S:13.02%.

IR (KBr): 3130, 2910, 2955, 2520, 1778, 1450, 1427, 1364, 1300, 1265, 1190, 1122, 875, k30, 819, 784 and 740 $cm^{-1}$.

KMR ($CD_3COOD$):1.16 (t,3H), 2.55 (s,3H), 3.1 (q,2H), 3.65 (t,3H), 4.9 (t,3H) and 8.0 (s,1N) ppm.

EXAMPLE 4:

1-[2'-(Ethylsulfonyl)-butyl]-2-methyl-5-Nitroimidazole

Following the procedure of Example 3, using the sodium salt of the butyl sulfonic acid in place of the ethyl sulfonic acid, the corresponding product is obtained, which is recrystallized from toluene (M.P. 93°-94.5° C.)

EXAMPLE 5:

1-[2'-(Ethylsulfonyl)-ethyl]-2-Ethyl-5-Nitroimidazole

Following the procedure of Example 3, and using 1-(2'-bromoethyl)-2-ethyl-5-nitroimidazole, as the starting material, there is obtained the corresponding product, M.P. 130°-140° C.

EXAMPLE 6:

1-[2'-(Ethylsulfonyl)-Ethyl]-2-Methyl-5-Nitroimidazole 2.25 g. (8 m moles) of 1-(2'-iodoethyl)-2-methyl-5-nitroimidazole is dissolved in 40 ml. of dimethylformamide and while stirring at 60° C., 2.79 g. (24 m moles) of sodium ethylsulfinate ($NaSO_2C_2H_5$) is added during 2½ hours. The reaction mixture then is stirred for 3 hours at 60° C. and the dimethylformamide is distilled under vacuum (24 to 25°, 0.7 mm Hg). The residue is dissolved in 40 ml. of water and extracted with 4 × 40 ml. portions of ethyl acetate. The extract is dried over $Na_2SO_4$ and vaporized. The oily residue spontaneously crystallized into crystals which are suspended in benzene and filtered with suction 1.174 g (59.2%) of 1-[2'-(ethylsulfonyl)-ethyl]-2-methyl-5-nitroimidazole is obtained, M.P. 122°-126° C. After recrystallization from 96% ethanol, the melting point is increased to 124.5°-126.5° C.

Analysis: $C_8H_{13}N_3O_4S$(MW247.27)—
Calculated: C 38.86, H 5.30, N 16.99%.
Found: C 39.10, H 5.60, N 16.82%.
IR-Spectrum (KBr): 3130 (m), 1520 (m), 1450 (s), 1365 (s), 1300 (s), 1265 (s), 1190 (s), 1120 (s), 1038 (m), 945 (m), 885 (m), 830 (m), 820 (m), 785 (m) and 742 (m) $cm^{-1}$.

We claim:

1. A process for making derivatives of 5-nitroimidazoles of the formula I:

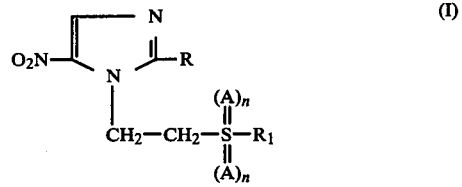

wherein
R is alkyl having 1-4 carbon atoms,
$R_1$ is alkyl having 1-4 carbon atoms,
A is oxygen, and
n is 1,
which comprises reacting a compound having the formula II:

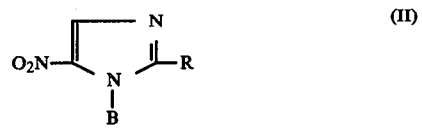

wherein
R is as defined in Formula I,
B is a 2'-haloethyl group ($CH_2CH_2Hal$), where Hal is a halogen atom, or an ethylsulfino group (—$CH_2CH_2SO_2H$) in the form of its alkali or alkaline earth salts, with compounds of the formula III:

wherein
(a) when B is 2'-haloethyl as defined above, Z is —$SO_2$—M wherein M is a metal selected from the group consisting of an alkali metal and an alkaline earth metal and $R_1$ is as defined above,
(b) when B is —$CH_2CH_2SO_2M$ wherein M is as defined above,
Z is halo as defined above and $R_1$ is as defined above, and
wherein said reactions are carried out in dimethylformamide.

2. A process according to claim 1, in which 1-[2'-ethylsulfonyl)-ethyl]-2-methyl-5-nitroimidazole is formed by reaction between 1-(2'-bromoethyl)-2-methyl-5-nitroimidazole and sodium ethyl sulfinic acid, and isolation of the desired product.

3. A method according to claim 1, in which 1-[2'-ethylsulfonyl)-ethyl]-2-methyl-5-nitroimidazole is formed by reaction between 1(2'-iodoethyl)-2-methyl-5-nitroimidazole and sodium ethyl sulfinate, and isolation of the desired product.

* * * * *